(12) United States Patent
Yamin (10) Patent No.: US 11,746,913 B2
(45) Date of Patent: *Sep. 5, 2023

(54) COLOR CHANGING AND PRESSURE SENSING CHECK VALVES

(71) Applicant: CareFusion 303, Inc., San Diego, CA (US)

(72) Inventor: Leyla Yamin, San Diego, CA (US)

(73) Assignee: CAREFUSION 303, INC., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/076,971

(22) Filed: Dec. 7, 2022

(65) Prior Publication Data

US 2023/0099255 A1 Mar. 30, 2023

Related U.S. Application Data

(63) Continuation of application No. 17/508,622, filed on Oct. 22, 2021, now Pat. No. 11,560,960, which is a continuation of application No. 17/037,450, filed on Sep. 29, 2020, now Pat. No. 11,187,333.

(51) Int. Cl.
*F16K 15/14* (2006.01)
*F16K 37/00* (2006.01)
*A61M 39/24* (2006.01)

(52) U.S. Cl.
CPC ........ *F16K 15/144* (2013.01); *F16K 37/0058* (2013.01); *A61M 39/24* (2013.01)

(58) Field of Classification Search
CPC ... A61M 39/24; F16K 15/144; F16K 37/0058
See application file for complete search history.

(56) References Cited

U.S. PATENT DOCUMENTS 3,241,514 A 3/1966 Grimland
3,780,693 A 12/1973 Parr
3,889,710 A 6/1975 Brost
(Continued)

OTHER PUBLICATIONS

Chu, "Engineers design color-changing compression bandage," May 29, 2018, retrieved from https://news.mit.edu/2018/color-changing-compression-bandage-signal-pressure-level-0529, 6 pages.
(Continued)

*Primary Examiner* — Patrick C Williams
(74) *Attorney, Agent, or Firm* — Morgan, Lewis & Bockius LLP (57) ABSTRACT

A check valve includes an upper housing defining an inlet of the check valve, and a lower housing having a seating portion and defining an outlet of the check valve. The check valve further includes a chamber interposed between and defined by the upper and lower housings for fluidly connecting the inlet and the outlet, and a flexible diaphragm mounted in the chamber. The flexible diaphragm selectively permits fluid flow in a first direction, and prevents fluid backflow in a second direction opposite to the first direction. The flexible diaphragm includes a color changing material, and when the flexible diaphragm is seated on the seating portion and bent due to force of the fluid flowing in the first direction, the flexible diaphragm exhibits a color change.

20 Claims, 4 Drawing Sheets

(56) References Cited

U.S. PATENT DOCUMENTS

| | | | |
|---|---|---|---|
| 4,712,583 | A | 12/1987 | Pelmulder |
| 5,581,978 | A | 12/1996 | Hekal |
| 8,162,006 | B2 | 4/2012 | Guala |
| 2007/0163656 | A1 | 7/2007 | Mijers |
| 2010/0294373 | A1* | 11/2010 | Haller ................ F16K 37/0041 |
| | | | 137/554 |
| 2011/0108147 | A1 | 5/2011 | Carmody |
| 2012/0004623 | A1 | 1/2012 | Tumminaro et al. |
| 2013/0167952 | A1 | 7/2013 | Mattson |

OTHER PUBLICATIONS

International Search Report and Written Opinion for Application No. PCT/US2021/052238, dated Jan. 25, 2022, 13 pages.

Pan, et al., "An ultra-sensitive resistive pressure sensor based on hollow-sphere microstructure induced elasticity in conducting polymer film," Nature Communications, Jan. 2014, retrieved from file://cpv-ctx-prd005/rdsfolder_us_west$/MP076463/Downloads/ncomms4002.pdf, 8 pages.

\* cited by examiner

COLOR CHANGING AND PRESSURE SENSING CHECK VALVES

CROSS-REFERENCE TO RELATED APPLICATIONS

This application is a continuation application of U.S. patent application Ser. No. 17/508,622, filed on Oct. 22, 2021, entitled "COLOR CHANGING AND PRESSURE SENSING CHECK VALVES," which issued as U.S. Pat. No. 11,560,960 on Jan. 24, 2023, which is a continuation application of U.S. patent application Ser. No. 17/037,450, filed on Sep. 29, 2020, entitled "COLOR CHANGING AND PRESSURE SENSING CHECK VALVES," which issued as U.S. Pat. No. 11,187,333, on Nov. 30, 2021, the disclosures of each are hereby incorporated by referenced in their entirety.

TECHNICAL FIELD

The present disclosure generally relates to check valves, and more particularly to valve members of check valves capable of changing color to visually indicate patency when subject to pressure from fluid flow.

BACKGROUND

Infusion IV sets are generally used in infusion therapy in order to deliver medication from a pre-filled container, e.g., an IV bottle or bag containing the desired medication, to a patient. Generally, the IV tubing is connected to a catheter and inserted into the localized area to be treated.

Patients are commonly injected with IV solutions that are initially provided in the IV bottle or bag and dripped into the vein of the patient through an IV line. Typically, an injection port is provided along the IV line and adapted to function with a syringe to permit an injectate to be added to the IV solution. A check valve is also commonly included in the IV line to permit fluid flow only in the direction of the patient. This ensures that the injectate flows downstream toward the patient, not upstream toward the IV reservoir.

In order to check for patency of conventional check valves, the IV line currently has to be opened in order to access and examine the check valve.

The description provided in the background section should not be assumed to be prior art merely because it is mentioned in or associated with the background section. The background section may include information that describes one or more aspects of the subject technology.

SUMMARY

One or more embodiments of a check valve include an upper housing defining a fluid inlet and having an internal surface, the internal surface including a first portion defining a ceiling and a second portion defining sidewalls of a chamber, each sidewall having a convex shape. The check valve also includes a fluid outlet, a chamber fluidly connecting the fluid inlet and the fluid outlet, and a flexible diaphragm disposed in the chamber, the flexible diaphragm having a color changing material configured to exhibit a color change when the flexible diaphragm is one of bent, bowed and deformed by a fluid flow from the fluid inlet.

One or more embodiments of an intravenous (IV) set include a drip chamber configured to be fluidly coupled to a fluid source and a check valve fluidly coupled to the drip chamber. The check valve includes an upper housing defining a fluid inlet and having an internal surface, the internal surface having a first portion defining a ceiling and a second portion defining sidewalls of a chamber, each sidewall having a convex shape. The check valve also includes a fluid outlet, a chamber fluidly connecting the fluid inlet and the fluid outlet, and a flexible diaphragm disposed in the chamber, the flexible diaphragm comprising a color changing material configured to exhibit a color change when the flexible diaphragm is one of bent, bowed and deformed by a fluid flow from the fluid inlet.

One or more embodiments of an intravenous (IV) set include a primary fluid system, a first drip chamber coupled to the primary fluid system, a secondary fluid system, a second drip chamber coupled to the secondary fluid system, and a check valve coupled to the first drip chamber and to the second drip chamber. The check valve includes an upper housing defining a fluid inlet and having an internal surface, the internal surface having a first portion defining a ceiling and a second portion defining sidewalls of a chamber, each sidewall having a convex shape. The check valve also includes a fluid outlet, a chamber fluidly connecting the fluid inlet and the fluid outlet, and a flexible diaphragm disposed in the chamber, the flexible diaphragm comprising a color changing material configured to exhibit a color change when the flexible diaphragm is one of bent, bowed and deformed by a fluid flow from the fluid inlet.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to check valves, and more particularly, for example and without limitation, to check valves capable of changing color to visually indicate patency when subject to pressure from fluid flow.

In accordance with some embodiments, a check valve includes an upper housing defining an inlet of the check valve, a lower housing defining an outlet of the check valve, and a chamber interposed between and defined by the upper and lower housings for fluidly connecting the inlet and the outlet. A flexible diaphragm may be mounted in the chamber to selectively permit fluid flow from the inlet to the outlet, and to prevent fluid backflow (reverse flow) from the outlet to the inlet.

In some embodiments, the flexible diaphragm may be in the form of a disc or any other circular plate and may be formed of a color changing material. When the flexible diaphragm is seated on a support portion of the lower housing and bent or bowed due to pressure of the fluid flowing in the direction from the inlet to the outlet, the flexible diaphragm may change color. Structurally, the flexible diaphragm may be formed of a plurality of stacked layers of transparent material. When the flexible diaphragm is exposed to an upstream pressure (i.e., a pressure applied by a fluid flowing from the inlet to the outlet), the flexible diaphragm bends, bows, or is otherwise deformed such that light reflects off each interface between adjacent layers of the flexible diaphragm. The reflected light produces colors in the visible spectrum on the flexible diaphragm that may be observed by a user/caregiver as an indication of fluid flow, thereby signaling patency of the check valve.

In some embodiments, the upper housing includes an internal surface defining sidewalls of the chamber. The sidewalls may have a convex shape which acts as a magnifying lens and allows for the color change of the flexible diaphragm to be magnified and more easily viewable.

Advantageously, due to the convex-shaped structure of the inner walls of the upper housing forming a magnifying lens, the color change of the flexible diaphragm can be easily viewed from the exterior without having to open the fluid line. The color change indicates patency of the check valve and may confirm to the user or caregiver that fluid is actually flowing through the check valve as intended. Further advantageously, the user or caregiver can confirm that there is a net upstream pressure (thereby indicating there is flow through the check valve) by simply observing the visual color change of the flexible diaphragm. As such, the need for a separate pressure sensor to confirm fluid flow is removed.

Figure 1:
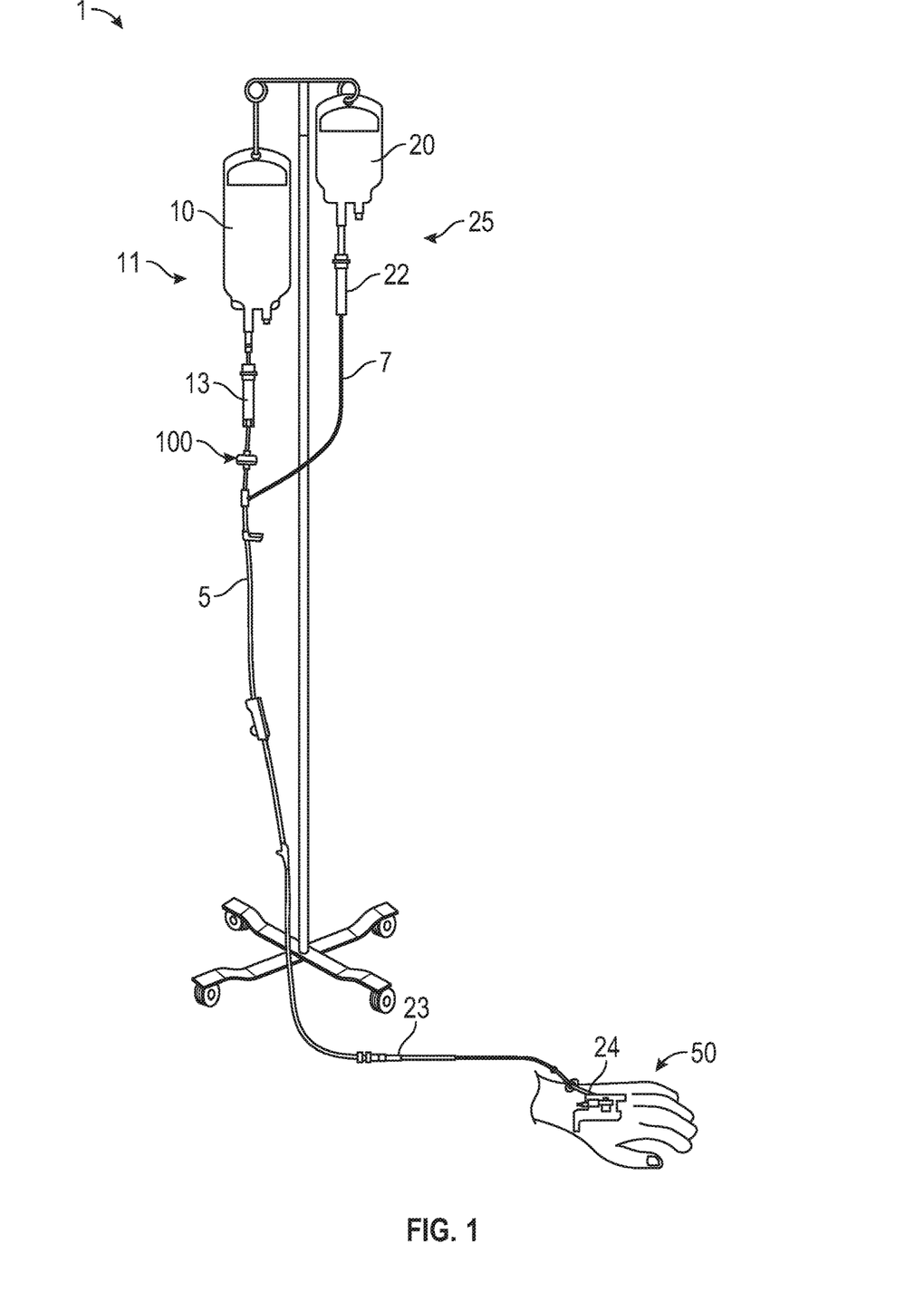
FIG. 1 illustrates an IV extension set that includes a check valve, in accordance with some embodiments of the present disclosure.

FIG. 1 illustrates an IV extension set that includes a check valve 100, in accordance with some embodiments of the present disclosure. As depicted, IV set 1 includes a primary fluid system 11 and a secondary fluid system 25. An IV pump (not shown) receives fluid from primary fluid system 11 and secondary fluid system 25 via a primary IV line 5 and may control and dispense the fluids therefrom to a patient 50.

In some embodiments, primary fluid system 11 may include a primary fluid source such as a primary fluid bag 10 which may include or contain saline solution or other medicinal fluid or drug to be administered to the patient 50. As illustrated, primary IV line 5 carries primary fluid from a drip chamber 13 to check valve 100. As shall be described further with respect to the following figures, check valve 100 may be disposed in primary IV line 5 and allow fluid flow from primary fluid bag 10 to the IV pump (not illustrated) while preventing reverse flow (backflow) of fluid from secondary fluid system 25 toward primary fluid bag 10. In accordance with some embodiments, secondary fluid system 25 includes secondary fluid source such as a secondary fluid bag 20, which may contain drugs or other secondary fluid to be supplied to the patient 50 for treatment. As depicted, the IV set 1 may further include a secondary IV line 7 which carries flow from drip chamber 22 to the check valve 100.

Figure 2:
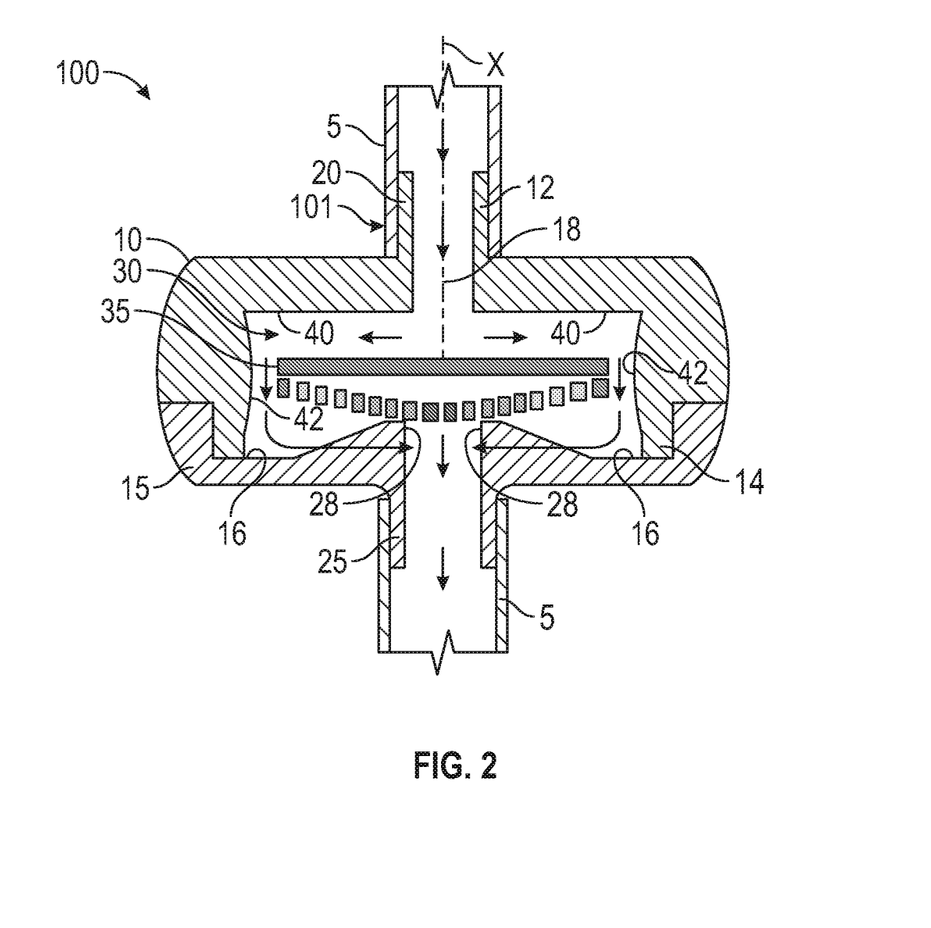
FIG. 2 illustrates a cross-sectional view of a check valve in an open state, in accordance with some embodiments of the present disclosure.

FIG. 2 illustrates a cross-sectional view of a check valve in an open state, in accordance with some embodiments of the present disclosure. Referring to FIG. 2, the check valve 100 may include an axially extending body 101 defining a central longitudinal axis X. In some embodiments, the body 101 may be formed of a chemical resistant material which may have magnifying properties. The body 101 may be formed of a material capable of providing superior light transmittance and clarity. For example, in some embodiments, the material of the body may be formed of an acrylic polymer. The body 101 may be a generally cylindrical (or tubular) structure and may include an upper housing 10 and a lower housing 15. The upper housing 10 may include a first end portion 12 and an axially opposite second end portion 14. As illustrated, a radial extent of the upper housing 10 at the second end portion 14 may be greater than the radial extent thereof at the first end portion 12. The lower housing 15 may include an upstream internal surface 16, and the second end portion 14 and the upstream internal surface 16 of the lower housing 15 may axially contact each other to co-operatively form a chamber 30 of the check valve 100.

In some embodiments, the upper housing 10 may include an inlet 20 of the check valve 100 at the first end 12, and the lower housing 15 may include an outlet 25 of the check valve 100. The body 101 may define an internal flow passage 18 axially extending between the inlet 20 and the outlet 25 and in fluid communication therewith. As is understood, the check valve 100 may permit fluid to flow from the inlet 20 to the outlet 25 (as indicated by the arrows in FIG. 2), and minimize, or otherwise limit, fluid flow from the outlet 25 to the inlet 20 (as indicated by the arrows in FIG. 5). As depicted, the upper housing 10 and the lower housing 15 may define the chamber 30 for fluidly connecting the inlet 20 and the outlet 25.

Figure 3:
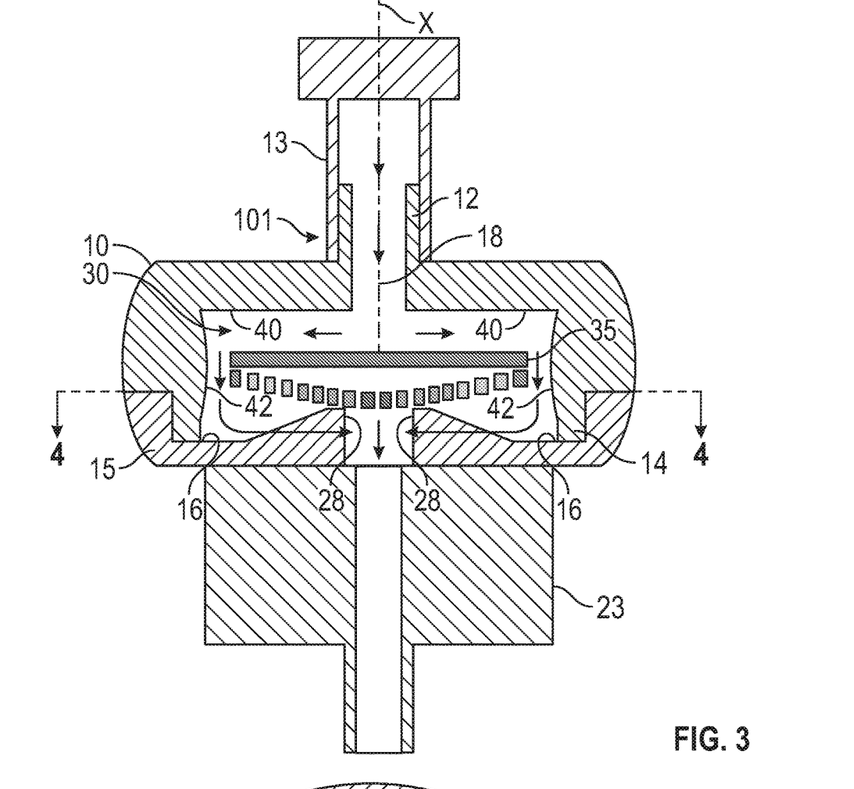
FIG. 3 illustrates a cross-sectional view of a check valve coupled to a male luer, in accordance with some embodiments of the present disclosure.
Figure 4:
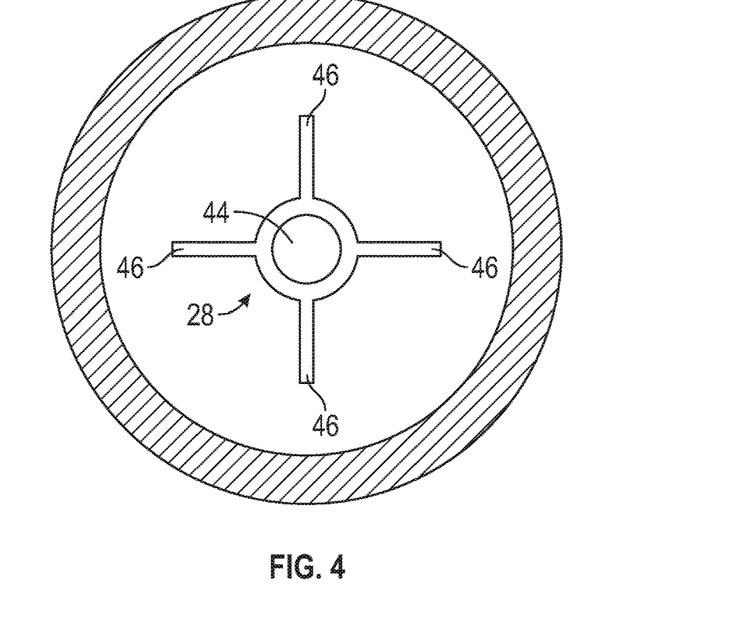
FIG. 4 illustrates a cross-sectional view of the check valve of FIG. 3 along line 4-4, in accordance with some embodiments of the present disclosure.

FIG. 3 illustrates a cross-sectional view of a check valve coupled to a male luer, in accordance with some embodiments of the present disclosure. FIG. 4 illustrates a cross-sectional view of the check valve of FIG. 3 along line 4-4, in accordance with some embodiments of the present disclosure. The check valve 100 of the various embodiments described herein may be positioned at different locations on the IV set 1, depending on the desired purpose. For example, in some embodiments the check valve 100 may be positioned below the drip chamber 13 to prevent any potential backflow into the primary IV line 5. In some embodiments, as depicted in FIG. 3, the check valve 100 may be built into or otherwise coupled to a connector, e.g., male luer connector 23 at the end of the IV set, closer to the patient 50. When coupled to the connector 23, the check valve 100 may be used to prevent backflow of the patient's blood into the IV set 1.

In the depicted embodiments, a flexible diaphragm 35 may be mounted in the chamber 30 to selectively permit fluid flow from the inlet 20 to the outlet 25, and prevent fluid backflow (reverse flow) from the outlet 25 to the inlet 20.

In accordance with some embodiments, the flexible diaphragm 35 may be in the form of a disc or any other circular plate. As depicted, the flexible diaphragm 35 may be mounted on a support portion 28 of the lower housing 14. In particular, the support portion 28 may include a central aperture 44 and a plurality of axially extending slots 46 through which fluid flowing from the inlet 20 and into the cavity 30 may enter the outlet 25 in the open state of the check valve 100.

As depicted, the flexible diaphragm 35 may be formed of a color changing material. As referred to herein a color changing material is defined as a material that, when subject to an axial load, is capable of reflecting light to exhibit vibrant colors in the visible spectrum. Accordingly, when the flexible diaphragm 35 is seated on the support portion 28 and bent due to force of the fluid flowing in the direction from the inlet 20 to the outlet 25, the flexible diaphragm 35 changes or otherwise exhibits color. In particular, in some embodiments, the flexible diaphragm 35 may be formed of a plurality of layers of transparent material. For example, the flexible diaphragm 35 may be formed of a plurality of ultrathin layers of the transparent materials, which may be periodically stacked to form the disc-shaped flexible diaphragm 35. In some embodiments, each layer of transparent material within the disc-shaped flexible diaphragm may be on the order of a few hundred nanometers thick. In some embodiments, the transparent material may be a transparent rubber material or any other similar material capable of bending or otherwise deforming under a load.

In some embodiments, the flexible diaphragm 35 may be formed of a resistive pressure sensing material having a hollow sphere microstructure such as, but not limited to an elastic, micro-structured conducting polymer thin film material.

In some embodiments, the flexible diaphragm 35 may be formed of a tactile pressure indicating sensor film. In yet other embodiments, the flexible diaphragm 35 may be formed of a material having hollow spheres in its structure, where the hollow spheres may be pressed together under pressure, causing the flexible diaphragm 35 to change color.

In some embodiments, the upper housing 10 includes an internal surface having a first portion defining a ceiling 40 and a second portion defining sidewalls 42 of the chamber 30. As depicted, the portion of the internal surface defining the sidewalls 42 may have a convex shape. Additionally, in some embodiments the sidewalls 42 are formed of a transparent material to allow for visual observation of the color change. Advantageously, the convex shape of the sidewalls 42 acts as a magnifying lens and allows for the color change of the flexible diaphragm 35 to be magnified and more easily observed.

In operation, when the flexible diaphragm 35 formed of the plurality of transparent layers is exposed to an upstream fluid pressure (i.e., a pressure applied by a fluid flowing from the inlet 20 to the outlet 25), the flexible diaphragm 35 may bend, bow or be otherwise deformed such that light reflects off each interface between adjacent layers of the flexible diaphragm. The reflected light produces colors in the visible spectrum on the flexible diaphragm 35 that may be dependent on the geometric properties and material composition of the transparent layers of the flexible diaphragm 35. For example, with layers of consistent thickness, the light reflected off the interfaces between the adjacent layers of the flexible diaphragm 35 may interact to strengthen some colors in the visible spectrum, for example red, while diminishing the brightness of other colors. Accordingly, when bent due to the upstream fluid pressure, the flexible diaphragm 35 formed of transparent layers may appear or otherwise exhibit a certain color, depending on the thickness of the layers within the flexible diaphragm 35.

In accordance with various embodiments, the flexible diaphragm 35 may be formed of a pressure sensing material. For example, the flexible diaphragm 35 may be made of a plurality of layered pressure-sensing photonic fibers such that when subject to the upstream pressure, for a specific desired pressure, the fibers of the flexible diaphragm 35 may reflect an easily distinguished color. To this effect, the flexible diaphragm 35 may be designed such that it changes color when the fluid flow from the inlet port to the outlet port exerts a pressure normal to the flexible diaphragm that is greater than or equal to a predetermined threshold pressure.

Accordingly, various embodiments of the present disclosure provide a check valve 100 having a flexible diaphragm 35 that changes color when bent, bowed, or otherwise deformed due to an upstream fluid pressure that is oriented substantially perpendicularly or normal to the flexible diaphragm 35. The upstream pressure causes the flexible diaphragm 35 to bend or bow outwards towards the outlet 25. As depicted, the flexible diaphragm 35 may bow outwards most at a central portion thereof where the fluid pressure is most concentrated or stronger. Once the flexible diaphragm 35 is bent or bowed while seated on the support portion 28, light reflects off each interface between adjacent layers of the flexible diaphragm 35. The reflected light produces colors in the visible spectrum on the flexible diaphragm 35.

In some embodiments, as illustrated in the figures, the color change may be most intense at a central portion of the flexible diaphragm where the fluid pressure is most concentrated and become less intense towards the outer periphery of the flexible diaphragm 35. For example, a caregiver may see different colors of different intensities depending on the magnitude of the upstream fluid pressure.

Advantageously, due to the convex-shaped structure of the inner walls 42 of the upper housing 10 which form a magnifying lens, the color change of the flexible diaphragm 35 can be easily viewed from the exterior without having to open the fluid line. The color change indicates patency of the check valve 100 and may confirm to the user or caregiver that fluid is actually flowing through the check valve 100 as intended. Further advantageously, the user or caregiver can confirm that there is a net upstream pressure (thereby indicating there is flow through the check valve 100) by simply observing the visual color change of the flexible diaphragm 35. As such, the need for a separate pressure sensor to confirm fluid flow is obviated.

Figure 5:
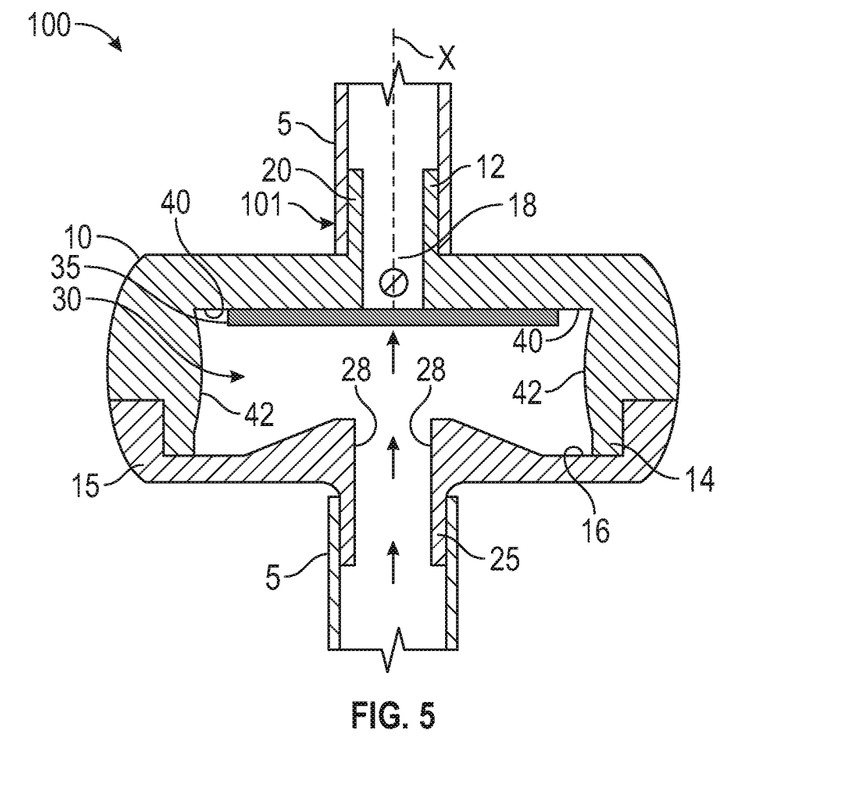
FIG. 5 illustrates a cross-sectional view of a check valve in a closed state, in accordance with some embodiments of the present disclosure.

FIG. 5 illustrates a cross-sectional view of a check valve 100 in a closed state, in accordance with some embodiments of the present disclosure. As depicted, and as previously described above, the upper housing 10 may include an internal surface having a first portion defining a ceiling 40 and a second portion defining sidewalls 42 of the chamber 30. In some embodiments, the ceiling 40 defines a sealing surface of the check valve 100. As illustrated in FIG. 5, in the closed state of the check valve 100, the flexible diaphragm 35 contacts the ceiling 40. Because the flexible diaphragm 35 contacts the internal surface defining the ceiling 40, reverse flow (backflow) of fluid from the outlet 25 to the inlet 20 is restricted or prevented.

During operation, when a downstream pressure (i.e., a pressure applied by a fluid flowing from the outlet 25 to the inlet 20) is applied to the flexible diaphragm 35, the flexible diaphragm 35 may be moved towards and contact the ceiling 40 to block fluid communication between the inlet 20 and the chamber 30, thereby restricting backflow of the fluid from the outlet 25 into the inlet 20. Preventing or restricting backflow of the fluid is advantageous in that it restricts undesirable particulate matter, for example, contained in a drug dispensed from a secondary path from flowing back through the flexible diaphragm 35, thereby preventing the patient from receiving the proper drug dosage concentration or from timely delivery of the drug.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve, comprising:
an upper housing defining a fluid inlet and having an internal surface, the internal surface comprising:
a first portion defining a ceiling; and
a second portion defining sidewalls of a chamber, each sidewall having a convex shape;
a fluid outlet;
a chamber fluidly connecting the fluid inlet and the fluid outlet; and
a flexible diaphragm disposed in the chamber, the flexible diaphragm comprising a color changing material configured to exhibit a color change when the flexible diaphragm is one of bent, bowed and deformed by a fluid flow from the fluid inlet.

2. The check valve of claim 1, wherein the flexible diaphragm comprises a plurality of periodically stacked layers of a transparent material.

3. The check valve of claim 2, wherein when the flexible diaphragm is one of bent, bowed and deformed, light reflects off each interface between adjacent layers of the flexible diaphragm to produce a color in the visible spectrum on the flexible diaphragm based on geometric properties and material composition of the transparent layers.

4. The check valve of claim 1, wherein the flexible diaphragm comprises a transparent rubber material.

5. The check valve of claim 1, wherein the flexible diaphragm comprises pressure sensing photonic fibers.

6. The check valve of claim 1, wherein the flexible diaphragm comprises a resistive pressure sensing material.

7. The check valve of claim 6, wherein the resistive pressure sensing material comprises a hollow sphere microstructure.

8. The check valve of claim 6, wherein the resistive pressure sensing material comprises an elastic, micro-structured conducting polymer thin film material.

9. The check valve of claim 1, wherein the flexible diaphragm comprises a tactile pressure indicating sensor film.

10. The check valve of claim 1, wherein the flexible diaphragm comprises a material having hollow spheres that when pressed together under pressure cause the flexible diaphragm to change color.

11. The check valve of claim 1, wherein the flexible diaphragm is configured to change color when the fluid flow contacting the flexible diaphragm has a pressure greater than or equal to a predetermined pressure.

12. The check valve of claim 1, wherein the flexible diaphragm is configured to change color when subject to a compressive force oriented substantially perpendicular to the flexible diaphragm.

13. The check valve of claim 1, wherein the flexible diaphragm is configured to display a first intensity of a color at a first portion of the flexible diaphragm and to display a second intensity of the color at a second portion of the flexible diaphragm based on differing fluid pressure on each of the first and second portions of the flexible diaphragm.

14. The check valve of claim 1, wherein the sidewalls comprise a transparent material configured to provide external visual observation of the color change.

15. The check valve of claim 14, wherein the convex shape of the sidewalls comprises a magnifying material configured to provide enhanced visual observation of the color change.

16. The check valve of claim 1, wherein the ceiling defines a sealing surface, and wherein in a closed state of the check valve, the flexible diaphragm is configured to contact the sealing surface to one of restrict and prevent fluid flow from the fluid outlet through the fluid inlet.

17. The check valve of claim 1, further comprising:
a lower housing defining the fluid outlet and comprising a support portion, wherein the flexible diaphragm is configured to be seated on the support portion.

18. The check valve of claim 17, the support portion comprising:
a central aperture; and
a plurality of axially extending slots, wherein in an open state of the check valve, from the fluid inlet is configured to flow through the slots and enter the fluid outlet.

19. An intravenous (IV) set, comprising:
a drip chamber configured to be fluidly coupled to a fluid source; and
a check valve fluidly coupled to the drip chamber, the check valve, comprising:
an upper housing defining a fluid inlet and having an internal surface, the internal surface comprising:
a first portion defining a ceiling; and
a second portion defining sidewalls of a chamber, each sidewall having a convex shape;
a fluid outlet;
a chamber fluidly connecting the fluid inlet and the fluid outlet; and
a flexible diaphragm disposed in the chamber, the flexible diaphragm comprising a color changing material configured to exhibit a color change when the flexible diaphragm is one of bent, bowed and deformed by a fluid flow from the fluid inlet.

20. An intravenous (IV) set, comprising:
a primary fluid system;
a first drip chamber coupled to the primary fluid system;
a secondary fluid system;
a second drip chamber coupled to the secondary fluid system; and
a check valve coupled to the first drip chamber and to the second drip chamber, the check valve, comprising:
an upper housing defining a fluid inlet and having an internal surface, the internal surface comprising:
a first portion defining a ceiling; and
a second portion defining sidewalls of a chamber, each sidewall having a convex shape;
a fluid outlet;
a chamber fluidly connecting the fluid inlet and the fluid outlet; and
a flexible diaphragm disposed in the chamber, the flexible diaphragm comprising a color changing material configured to exhibit a color change when the flexible diaphragm is one of bent, bowed and deformed by a fluid flow from the fluid inlet.

\* \* \* \* \*